(12) United States Patent
Tozzi

(10) Patent No.: US 10,426,620 B2
(45) Date of Patent: Oct. 1, 2019

(54) APPARATUS AND METHOD TO RESHAPE GEOMETRY OF DISEASED HEART VALVE

(71) Applicant: Luigi P. Tozzi, Fort Collins, CO (US)

(72) Inventor: Luigi P. Tozzi, Fort Collins, CO (US)

(73) Assignee: MITRAL TECHNOLOGIES S.A., Liege (BE)

(*) Notice: Subject to any disclaimer, the term of this patent is extended or adjusted under 35 U.S.C. 154(b) by 0 days.

(21) Appl. No.: 15/109,437

(22) PCT Filed: Dec. 31, 2014

(86) PCT No.: PCT/US2014/073084
§ 371 (c)(1),
(2) Date: Jun. 30, 2016

(87) PCT Pub. No.: WO2015/103434
PCT Pub. Date: Jul. 9, 2015

(65) Prior Publication Data
US 2016/0317289 A1  Nov. 3, 2016

Related U.S. Application Data

(60) Provisional application No. 61/923,319, filed on Jan. 3, 2014.

(51) Int. Cl.
*A61B 17/12* (2006.01)
*A61F 2/24* (2006.01)
*A61B 17/00* (2006.01)

(52) U.S. Cl.
CPC ............ *A61F 2/246* (2013.01); *A61F 2/2445* (2013.01); *A61F 2/2451* (2013.01);
(Continued)

(58) Field of Classification Search
CPC .............................. A61F 2/2451; A61F 2/246
See application file for complete search history.

(56) References Cited

U.S. PATENT DOCUMENTS

2005/0004668 A1    1/2005  Aklog et al.
2005/0228422 A1*  10/2005  Machold .......... A61B 17/00234
                                                 606/167
(Continued)

OTHER PUBLICATIONS

PCT International Search Report dated Apr. 28, 2015 of International Application No. PCT/US14/73084. 10 Pages.

*Primary Examiner* — Yashita Sharma
*Assistant Examiner* — Rebecca S Preston
(74) *Attorney, Agent, or Firm* — Barcelo, Harrison & Walker LLP

(57) ABSTRACT

Devices and methods are disclosed for treating mitral valve regurgitation that include members that assist the valve in closing during the cardiac cycle. Such devices may include members configured to alter the shape of mitral valve annulus. In certain embodiments, one or more wires may be anchored on one extremity to an element positioned along the posterior part of the mitral annulus, in the coronary sinus, and on another extremity to an element along the anterior part of the mitral annulus, fibrous trigon. The reshaping of the mitral annulus may be accomplished by pulling the wire or wires. Reducing the length of the wire or wires may provide the displacement of the posterior leaflets towards the anterior, thereby increasing the coaptation surface for the valve leaflets and reducing the regurgitation.

8 Claims, 18 Drawing Sheets

(52) U.S. Cl.
CPC ............... *A61B 17/00234* (2013.01); *A61B 2017/00243* (2013.01); *A61F 2/2454* (2013.01); *A61F 2/2466* (2013.01); *A61F 2220/0025* (2013.01); *A61F 2220/0075* (2013.01); *A61F 2250/0004* (2013.01)

(56) References Cited

U.S. PATENT DOCUMENTS

| | | | |
|---|---|---|---|
| 2006/0020336 A1* | 1/2006 | Liddicoat | A61B 17/0644 623/2.37 |
| 2006/0030885 A1* | 2/2006 | Hyde | A61B 17/00234 606/232 |
| 2006/0252984 A1 | 11/2006 | Rahdert et al. | |
| 2010/0222876 A1 | 9/2010 | Hyde | |
| 2014/0277406 A1* | 9/2014 | Arcidi | A61F 2/2466 623/2.11 |

* cited by examiner

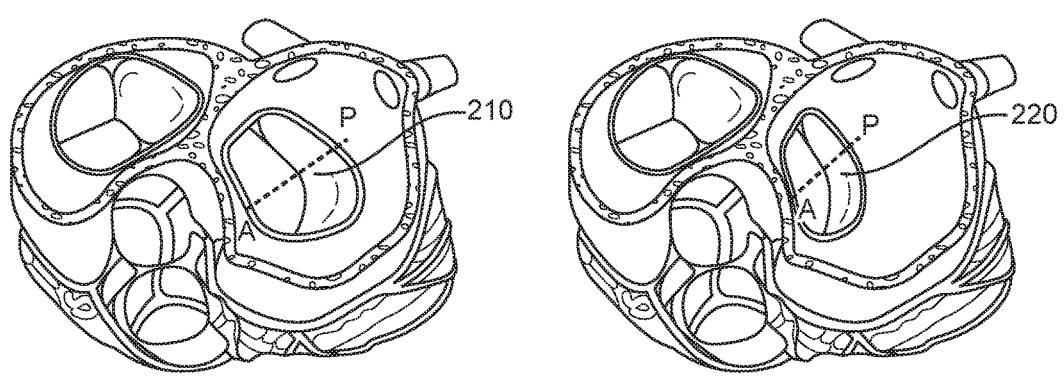
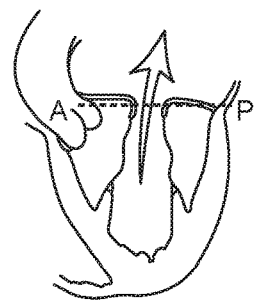
FIG. 2A
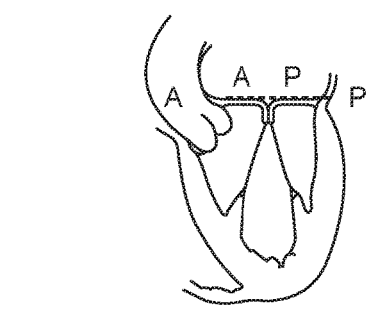
FIG. 2B

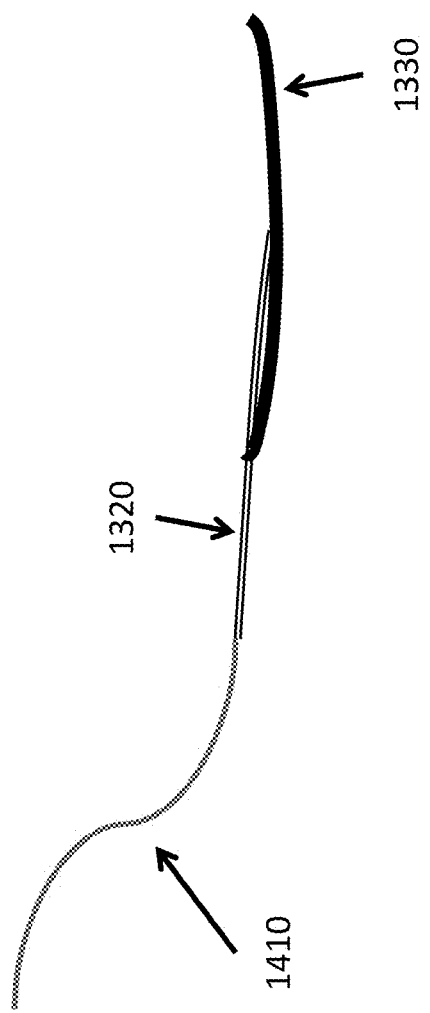

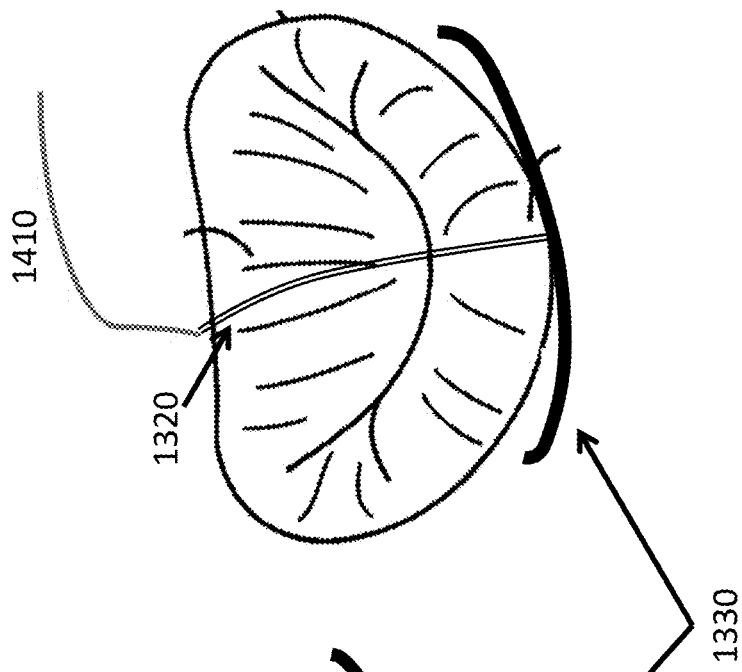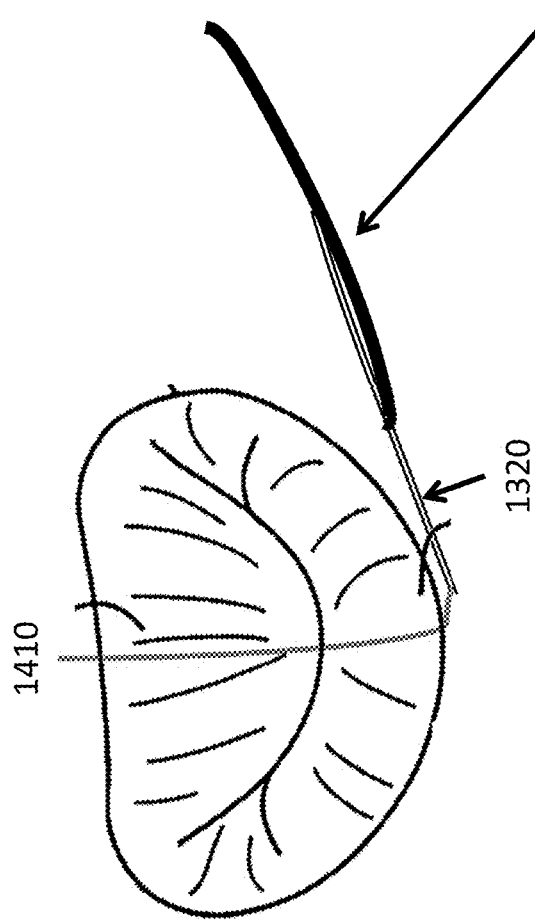

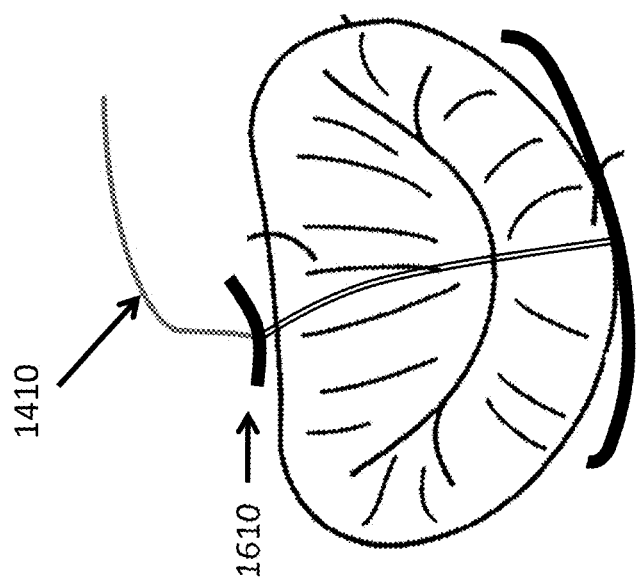

APPARATUS AND METHOD TO RESHAPE GEOMETRY OF DISEASED HEART VALVE

I. CROSS-REFERENCE TO RELATED APPLICATIONS

This application is the national stage for International Patent Cooperation Treaty Application PCT/US2014/073084, filed Dec. 31, 2014, which claims the benefit of U.S. Provisional Patent Application Ser. No. 61/923,319, entitled "Apparatus and method to reshape geometry of diseased heart valve," and filed on 3 Jan. 2014. The entirety of the foregoing patent applications is incorporated by reference herein.

II. TECHNICAL FIELD

The present disclosure relates to the repair and/or correction of dysfunctional heart valve. More particularly pertains to mitral valve regurgitation treatment using only endovascular techniques deploying devices that passively assist to close a heart valve to improve valve function.

II. BACKGROUND

A human heart has four chambers, the left and right atrium and the left and right ventricles. The chambers of the heart alternately expand and contract to pump blood through the vessels of the body. The cycle of the heart includes the simultaneous contraction of the left and right atria, passing blood from the atria to the left and right ventricles. The left and right ventricles then simultaneously contract forcing blood from the heart and through the vessels of the body. In addition to the four chambers, the heart also includes a check valve at the upstream end of each chamber to ensure that blood flows in the correct direction through the body as the heart chambers expand and contract. These valves may become damaged, or otherwise fail to function properly, resulting in their inability to properly close when the downstream chamber contracts. Failure of the valves to properly close may allow blood to flow backward through the valve resulting in decreased blood flow and lower blood pressure.

Mitral regurgitation occurs when the mitral valve separating the left atrium and the left ventricle fails to properly close. As a result, upon contraction of the left ventricle blood may leak or flow from the left ventricle back into the left atrium, rather than being forced through the aorta.

The mitral valve has 2 leaflets, anterior and posterior, both connected on one side to the mitral annulus and on the free edges to the cordae and cardiac muscle. In order to close properly, the free edges of the two leaflets have to touch each other over a length of several millimeters and this is called leaflets coaptation. Mitral regurgitation is mainly due to a lack of leaflets coaptation as a consequence of annulus dilatation or cardiac muscle dysfunction. Regardless of the cause, mitral regurgitation may result in a decrease in blood flow through the body (cardiac output) and deserve surgical treatment.

III. BRIEF DESCRIPTION OF THE DRAWINGS

FIGS. 1A-B depict cross-sectional views of a normal mitral valve and a regurgitant mitral valve in accordance with certain embodiments.

FIGS. 2A-B depict cross-sectional views of a regurgitant mitral valve and a reshaped mitral valve in accordance with certain embodiments.

Figure 10B:
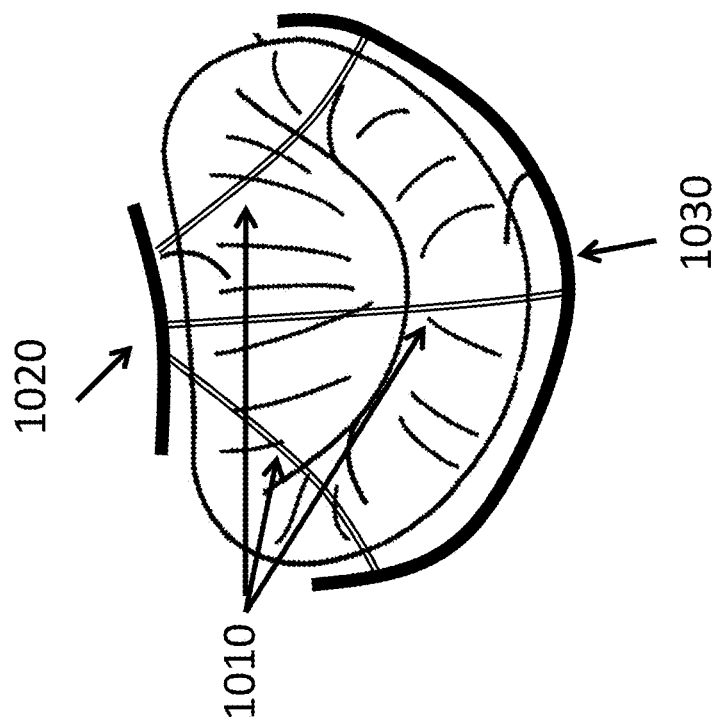
Figure 10A:
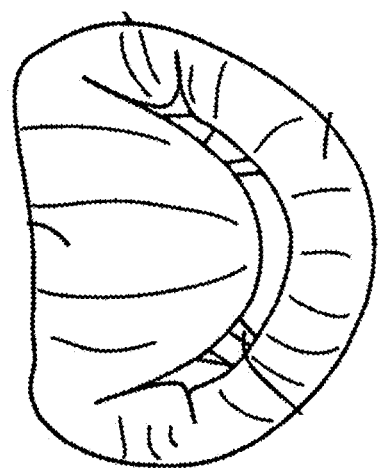

FIGS. 10A-B depict a method of installing three wires to increase leaflets coaptation in accordance with certain embodiments.

Figure 11:
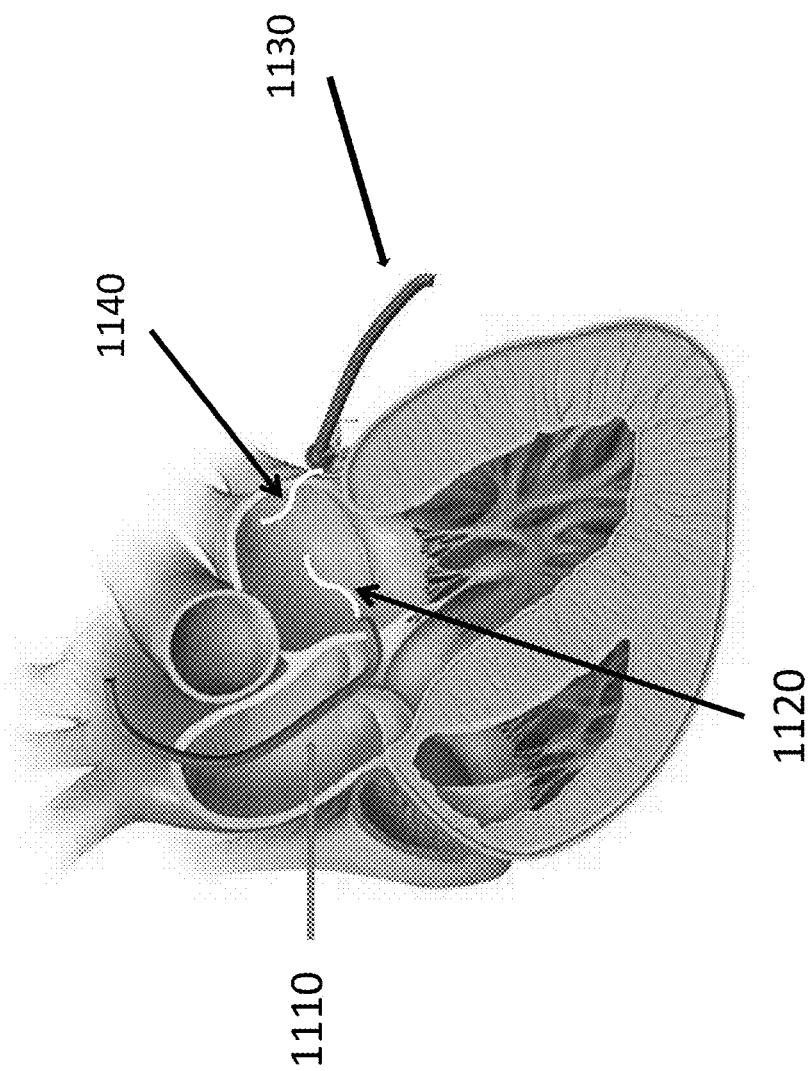

FIG. 11 depicts a method of installing wires into the trigon region in accordance with certain embodiments.

Figure 12:
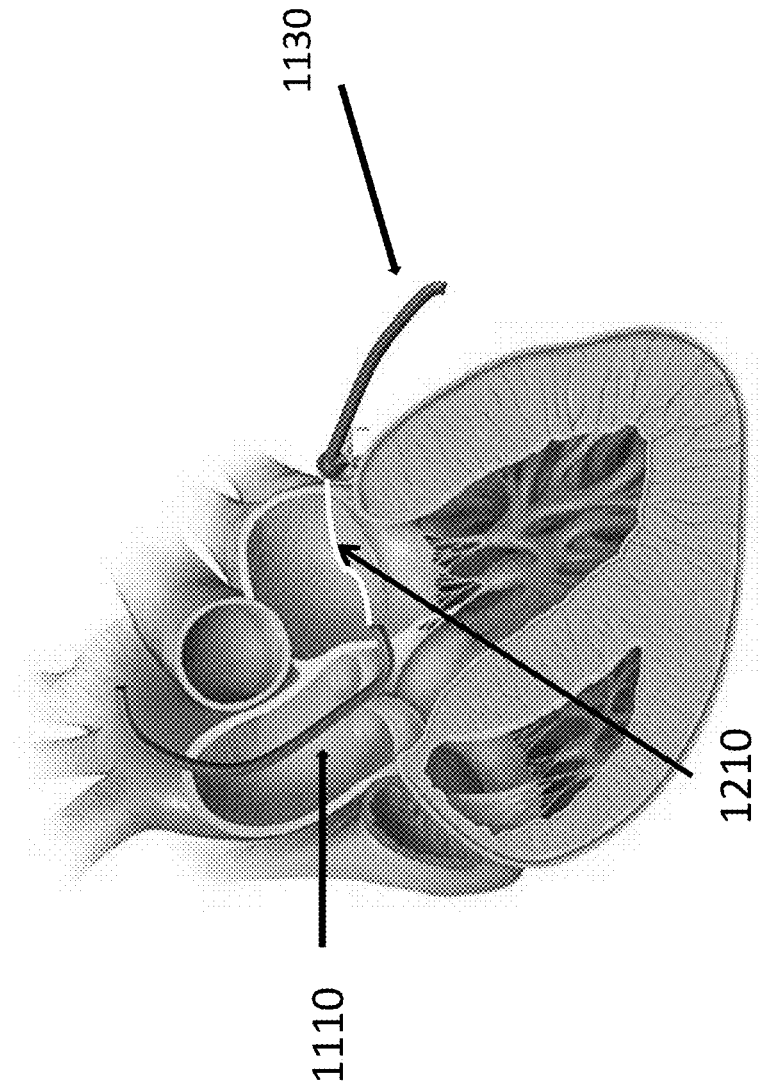

FIG. 12 depicts a method of coupling wires in the trigon region in accordance with certain embodiments.

Figure 13:
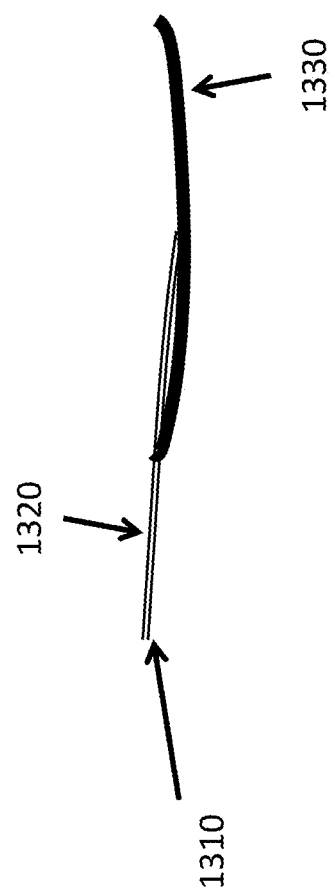

FIG. 13 depicts an assembled posterior holding element and connecting element in accordance with certain embodiments.

FIG. 14 depicts a method of connecting the free end of a connecting element to a wire exiting the femoral vein in accordance with certain embodiments.

FIGS. 15A-B depict a method of pulling a wire that exits the femoral artery until the assembled element reaches the coronary sinus in accordance with certain embodiments.

Figure 16:
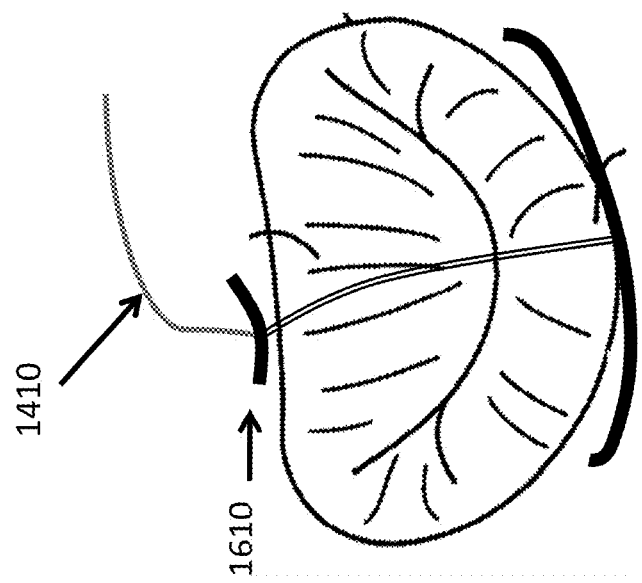

FIG. 16 depicts a method of positioning an anterior holding element below the aortic valve at the level of the fibrous trigon in accordance with certain embodiments.

FIG. 17 depicts a method of adjusting the connecting element length and locking the anterior holding element to the connecting element in accordance with certain embodiments.

Figure 18B:
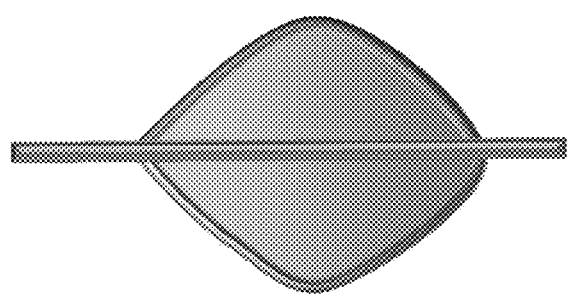
Figure 18A:

FIGS. 18A-B depict changing the profile of one or more wires during a cardiac cycle in accordance with certain embodiments.

IV. DETAILED DESCRIPTION

Devices and methods are disclosed for treating mitral valve regurgitation that include members that assist the valve in closing during the cardiac cycle. Such devices may include members configured to alter the shape of mitral valve annulus. In certain embodiments, one or more wires may be anchored on one extremity to an element positioned along the posterior part of the mitral annulus, in the coronary sinus, and on another extremity to an element along the anterior part of the mitral annulus, fibrous trigon. The reshaping of the mitral annulus may be accomplished by pulling the wire or wires. Reducing the length of the wire or wires may provide the displacement of the posterior leaflets towards the anterior, thereby increasing the coaptation surface for the valve leaflets and reducing the regurgitation.

In certain embodiments, an annuloplasty device is disclosed, comprising: a first holding element configured to be located in a coronary sinus of a heart; a second holding element configured to be located in a fibrous trigon of the heart; and one or more connecting elements for connecting the first holding element and the second holding element, the one or more connecting elements configured to pull the first holding element toward the second holding element to reduce the distance between an anterior portion of the mitral annulus of the heart and a posterior portion of the mitral annulus, thereby increasing mitral valve leaflets coaptation. The one or more connecting elements may be configured to cross the valve area on the atrial side. The first and second holding elements and the one or more connecting elements may be configured to be deployed into the heart using endovascular techniques. At least one of the one or more connecting elements may be configured to change its profile during a cardiac cycle to prevent mitral leaflets damage due to impingement of one or more mitral valve leaflets on the at least one connecting element during ventricular systole. At least one of the one or more connecting elements may be configured to change its profile during a cardiac cycle not to block blood flow from atrium to ventricle. A plurality of the one or more connecting elements may be configured to be joined in situ to form a single connecting element.

In certain embodiments, the first holding element may be configured to be located in a coronary sinus of a heart and one connecting element for connecting the first holding element and the second holding element, may be assembled with the first holding element into a single element before the implant.

In certain embodiments, a method of inserting an annuloplasty device is disclosed, comprising: placing a first holding element into a coronary sinus of a heart; connecting one or more connecting elements to the first holding element; pulling at least one of the one or more connecting elements to increase mitral valve leaflet coaptation; connecting the one or more connecting elements to a second holding element at the level of the mitro-aortic junction and fibrous trigon of a heart. The step of connecting one or more connecting elements to the first holding element may comprise placing one or more connecting elements through the mitro-aortic junction of a heart. The step of connecting the one or more connecting elements to the first holding element may comprise: piercing the left ventricle outflow tract at the level of fibrous trigon with a first connecting element; extending the first connecting element across a valve area towards the posterior mitral annulus of the heart; piercing the mitral annulus and the coronary sinus with the first connecting element and connecting the first connecting element to the first holding element. One of the one or more connecting elements may be placed in the left ventricle outflow tract at the level of the fibrous trigon, below the aortic valve using endovascular techniques. At least one of the one or more connecting elements may change its profile during a cardiac cycle to prevent mitral leaflet damage due to impingement of one or more mitral valve leaflets on the at least one connecting element during ventricular systole. At least one of the one or more connecting elements may change its profile during a cardiac cycle and may not block blood flow from atrium to ventricle. The method may further comprise adjusting the length of the connecting element. The step of adjusting the length of the connecting element may be performed during a selected one of an initial procedure to install the annuloplasty device and a later procedure after the initial procedure is completed.

In certain embodiments, a method of inserting an annuloplasty device is disclosed, comprising: connecting a first holding element to one or more connecting elements; placing the first holding element connected to the one or more connecting elements into the coronary sinus of the heart; connecting the one or more connecting elements to a second holding element placed at the level of the mitro-aortic junction and fibrous trigon of a heart; pulling at least one of the one or more connecting elements to increase mitral valve leaflets coaptation. The step of connecting the one or more connecting elements to the second holding element may comprise: piercing a coronary sinus of the heart with a first holding element connected to one or more connecting elements avoiding the circonflex artery of the heart; extending the first connecting element across a valve area towards the fibrous trigon on the atrial side of the valve; piercing the left ventricle outflow tract at the level of the fibrous trigon with the first connecting element; pulling at least one of the one or more connecting elements to increase mitral valve leaflets coaptation; and connecting the first connecting element to the second holding element. One of the one or more connecting elements may be placed in the left ventricle outflow tract at the level of the fibrous trigon, below the aortic valve using endovascular techniques. At least one of the one or more connecting elements may change its profile during a cardiac cycle to prevent mitral leaflet damage due to impingement of one or more mitral valve leaflets on the at least one connecting element during ventricular systole. At least one of the one or more connecting elements may change its profile during a cardiac cycle and may not block blood flow from atrium to ventricle. A plurality of the one or more connecting elements may be joined in situ to form a single connecting element.

Figure 1B:
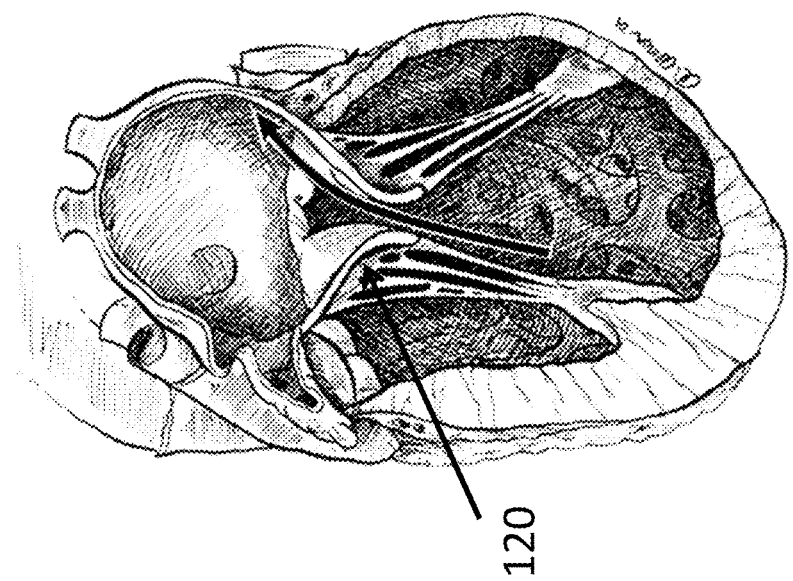
Figure 1A:
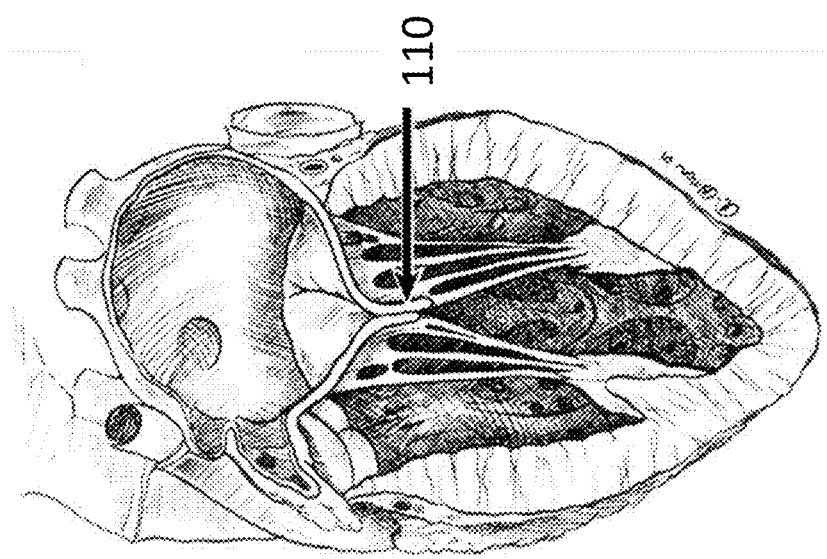

To reduce mitral regurgitation, certain embodiments increase leaflets coaptation by pulling the posterior annulus toward the anterior (FIGS. 1 and 2) using 2 holding elements and wires. FIG. 1A depicts a normal mitral valve 110, wherein leaflets coaptation allows the mitral valve to tightly seal. FIG. 1B depicts a regurgitant mitral valve 120 that lacks leaflets coaptation due to mitral annulus dilation, preventing the valve from achieving a tight seal. In certain embodiments, it is desired to reduce distance A-P as depicted in FIGS. 2A-B to improve leaflet coaptation in the mitral valve. FIG. 2A depicts distance A-P in regurgitant mitral valve 210, which FIG. 2B depicts reshaped mitral valve 220 with reduced distance A-P.

Figure 3:
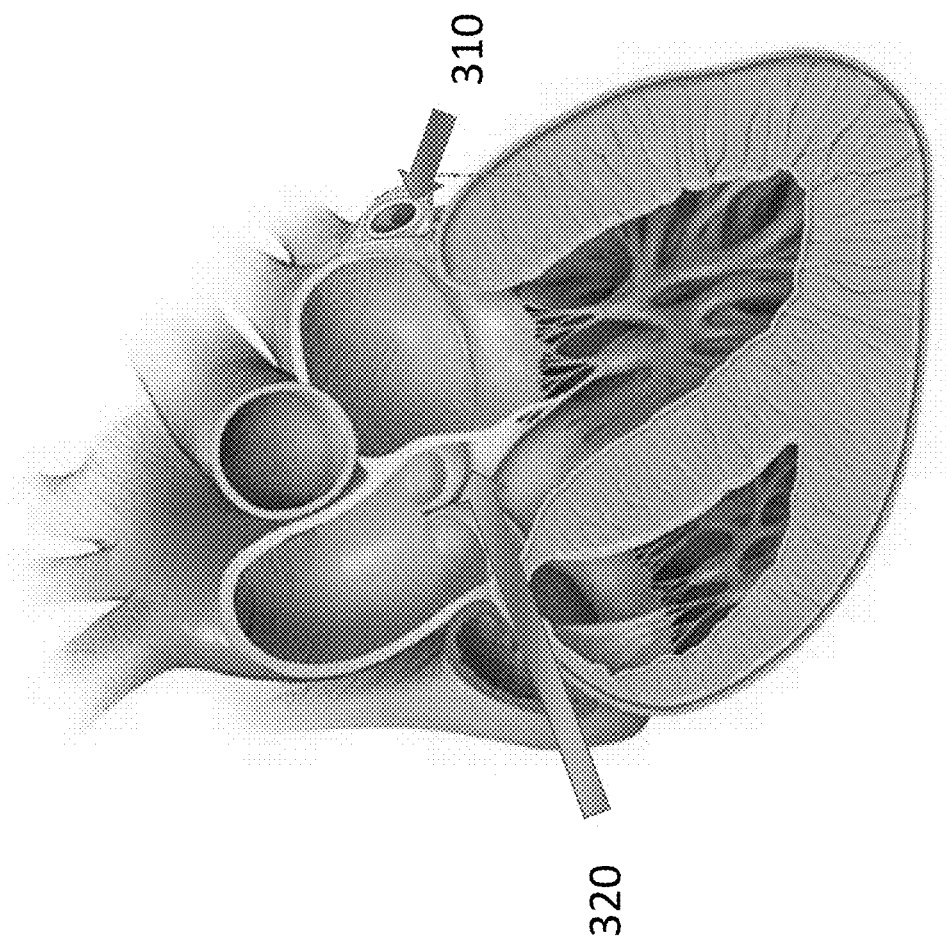
FIG. 3 depicts a cross-sectional view of a heart in accordance with certain embodiments.

In certain embodiments, the procedure can be totally endovascular, alleviating the need for open-heart surgery, and may utilize anatomical relationships between the mitral annulus, coronary sinus 310, fibrous trigon 320 and aortic valve as shown in FIG. 3.

Figure 4:
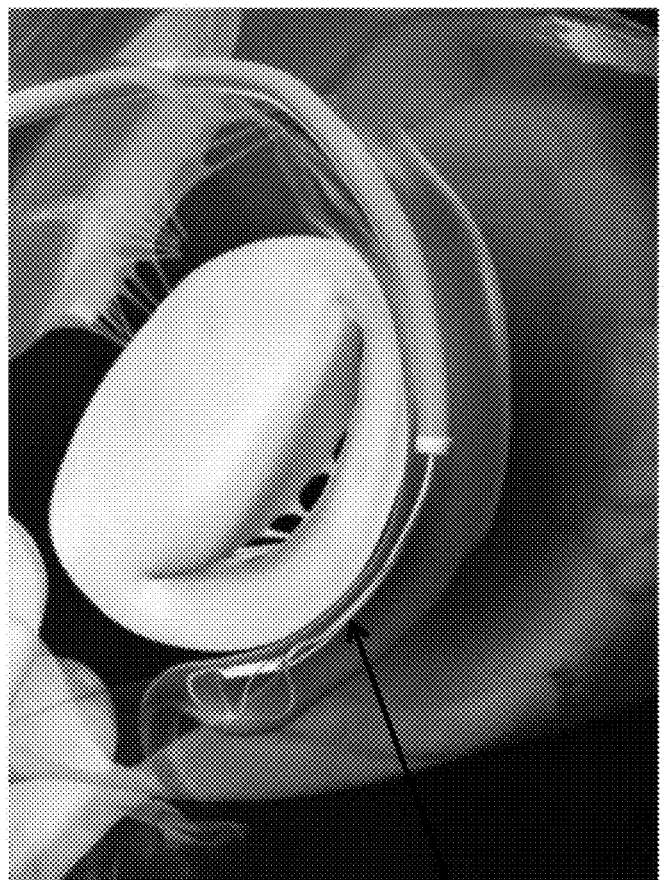
FIG. 4 depicts placement of a posterior holding element in accordance with certain embodiments.

In certain embodiments, the procedure may consist of 4 steps:

In certain embodiments as shown in FIG. 4, Step 1 may include insertion of posterior holding element into the coronary sinus through the femoral vein. An exemplary holding element 410 is shown and described in FIG. 4. The posterior holding element 410 may be a rod that reproduces the saddle shape of the posterior part of the mitral annulus. In certain embodiments, the posterior holding element 410 may be made of stainless steel, but one of ordinary skill in the art will recognize that other metals or polymers may be used. In certain embodiments, conventional techniques of placement may be used such as techniques known to one of ordinary skill in the art for positioning pacemaker electrodes and/or a Carillon device.

Figure 5:
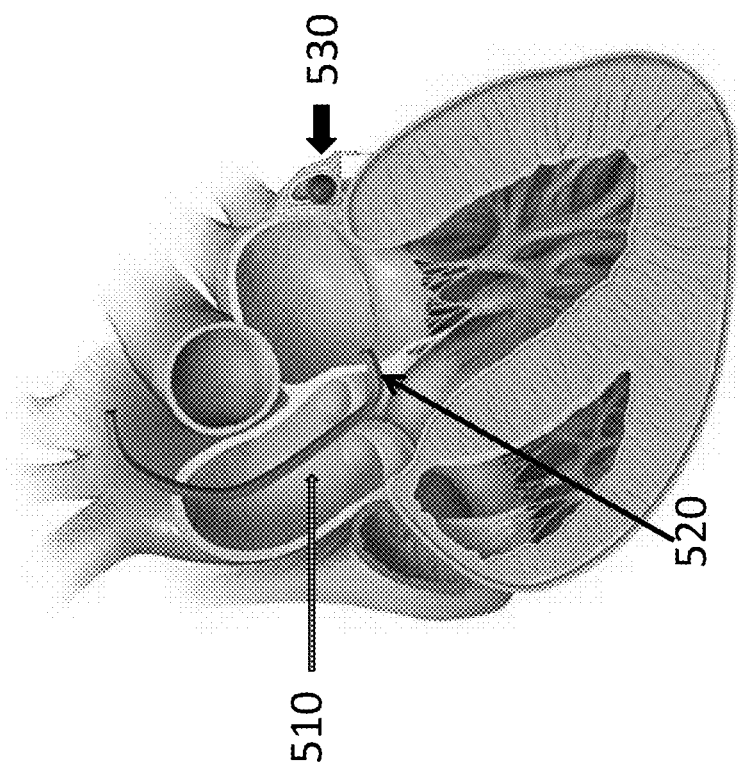
FIG. 5 depicts placement of an anterior holding element in accordance with certain embodiments.
Figure 6:
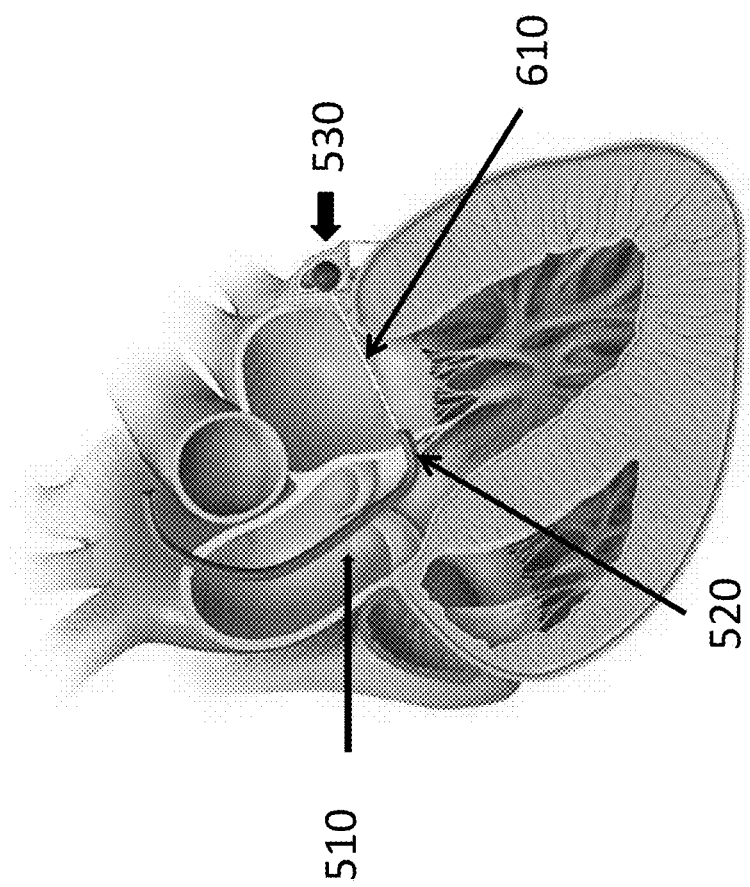
FIG. 6 depicts placement of one or more wires through the mitro-aortic junction in accordance with certain embodiments.

In certain embodiments as shown in FIG. 5, Step 2 may include placement of the wires through the fibrous trigon, which may be accomplished using existing transcatheter technology. A delivery catheter 510 may be inserted into femoral artery and advanced into the aorta, below the aortic valve at the level of the mitro-aortic junction (FIG. 5). The wire may be inserted into the delivery catheter 510. The wire may pierce the fibrous trigon 520 and may be directed toward the posterior holding element 530 under fluoroscopy control. In certain embodiments as shown in FIG. 6, the wire may pierce the posterior mitral annulus and may catch the posterior holding element 530 (FIG. 6). One of ordinary skill in the art will recognize that the posterior holding element may be attached to the wire prior to insertion via the catheter.

Figure 7:
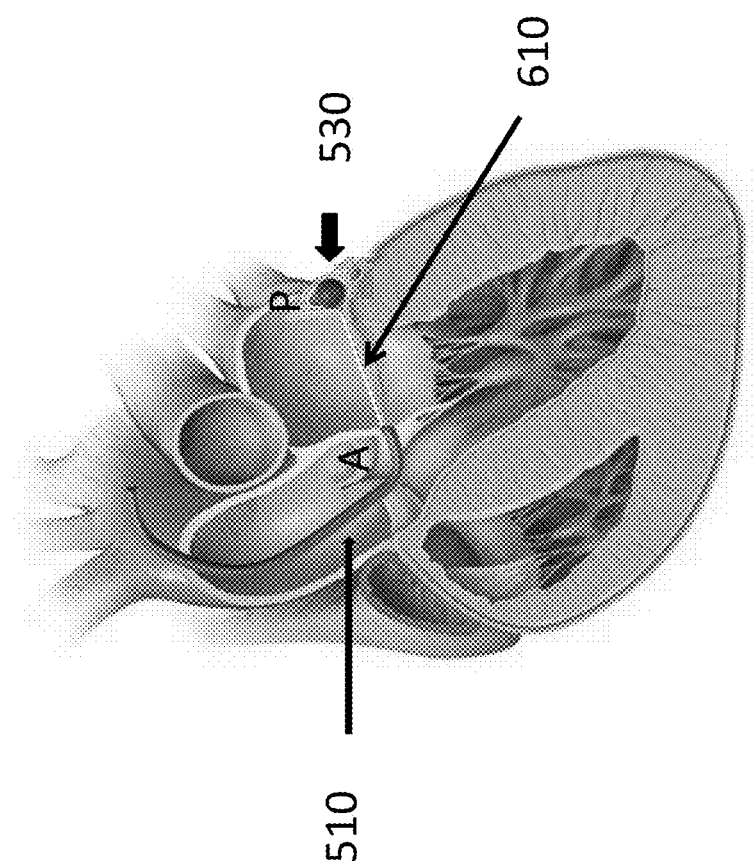
FIG. 7 depicts pulling the one or more wires through the mitro-aortic junction to correct mitral regurgitation in accordance with certain embodiments.

In certain embodiments as shown in FIG. 7, Step 3 may include pulling of the posterior holding element 530. Once the wire 610 is connected to the posterior holding element 530, the wire 610 may be pulled through the delivery catheter 510 to reduce the Antero-Posterior distance, thereby increasing leaflets coaptation and correcting mitral regurgitation.

Figure 8:
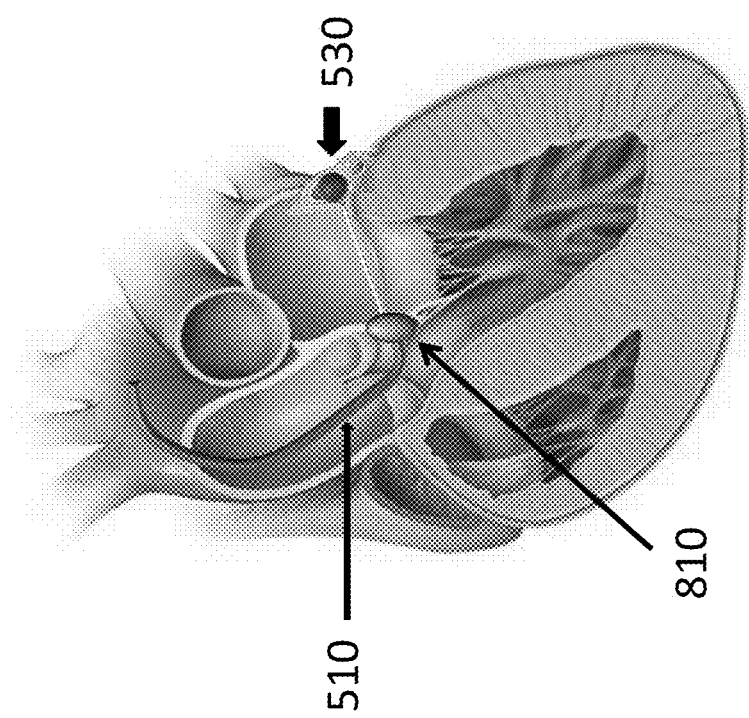
FIG. 8 depicts locking the one or more wires over an anterior holding element in accordance with certain embodiments.
Figure 9:
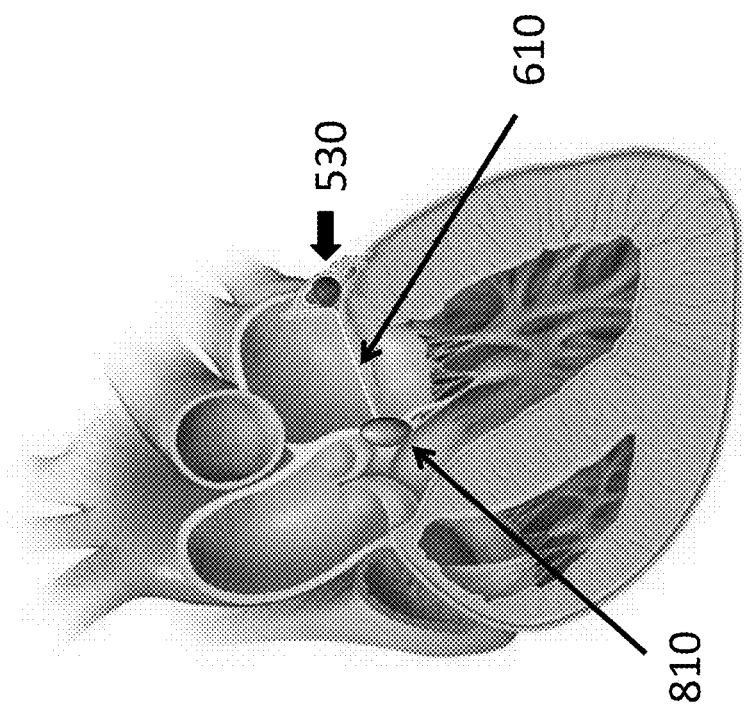
FIG. 9 depicts the one or more wires installed to increase leaflets coaptation in accordance with certain embodiments.

In certain embodiments as shown in FIG. 8, Step 4 may include locking wire 610 over anterior holding element 810. An anterior holding element 810 may be inserted into the delivery catheter 510. The anterior holding element 810 may have a rod shape and may be made of metal or polymer or other suitable materials known to those of skill in the art. The anterior holding element 810 may be placed at the level of the mitro-aortic junction. The wire may be locked over the anterior holding element 810. In certain embodiments as shown in FIG. 9, the delivery catheter 510 may be retrieved and the procedure completed.

The number of wires varies according to the severity of the mitral regurgitation. In FIGS. 10A and B, an embodiment with 3 wires 1010 is illustrated. FIG. 10A depicts a mitral valve exhibiting mitral regurgitation due to the absence of leaflet coaptation. FIG. 10B shows a mitral valve with three wires 1010 used to connect anterior holding element 1020 and posterior holding element 1030. One of ordinary skill in the art will recognize that the number of wires 1010 may be varied depending on the severity of the mitral regurgitation. In certain embodiments, steps 2-4 above may be repeated for each subsequent wire 1010 until the desired number of wires 1010 has been installed. Once the desired number of wires 1010 has been installed, the delivery catheter 510 may be retrieved and the procedure completed.

In certain embodiments, the procedure may consist of 5 steps:

In certain embodiments as shown in FIG. 11, Step 1 may include placement of the wires through the fibrous trigon, which may be accomplished without limitation using existing transcatheter technology or other methods known to those of skill in the art. A delivery catheter 1110 may be inserted into a femoral artery and advanced into the aorta, below the aortic valve at the level of the mitro-aortic junction as shown in FIG. 5. The wire 1120 may be inserted into the delivery catheter 1110. The wire 1120 may pierce the fibrous trigon and be kept floating in the left atrium In certain embodiments, Step 2 may include placement of the wires into the coronary sinus using existing transcatheter technology or other methods known to those of skill in the art. A delivery catheter 1130 may be inserted into the femoral vein and advanced into the coronary sinus (great cardiac vein). The wire 1140 may be inserted into the delivery catheter and advanced. The wire 1140 may pierce the wall of the left atrium at the level where the connecting element has to be placed. The wire 1140 may be kept floating in the left atrium.

In certain embodiments as shown in FIG. 12, Step 3 may include joining the wire 1120 coming from the fibrous trigon and wire 1140 coming from the coronary sinus (shown in FIG. 11), using magnetic coupling force or using other existing transcatheter technology such as snare wires. This action may result in having one single wire 1210 going from the femoral vein to the femoral artery trough the coronary sinus and fibrous trigon.

In certain embodiments as shown in FIGS. 13-15, Step 4 may include connection of the assembled device to the wire 1410 on the vein end. The free end 1310 of the connecting element 1320, the one to be connected to the holding element 1330 to be located in the fibrous trigon, is connected to the wire 1410 on the vein end as shown in FIGS. 13 and 14. Pulling the wire 1410 through the arterial end as shown in FIG. 15A may allow the positioning of assembled device into the coronary sinus first. Once the holding element 1330 to be located in the coronary sinus is in place as shown in FIG. 15B, the wire 1410 is pulled till the connecting element 1320 is completely deployed over the mitral valve and reaches the fibrous trigon, below the aortic valve as shown in FIG. 15B.

In certain embodiments as shown in FIG. 16, Step 5 may include locking the wire 1410 over anterior holding element 1610. An anterior holding element 1610 may be inserted into the delivery catheter. The anterior holding element 1610 may have a rod shape and may be made of metal or polymer or other suitable material known to those skilled in the art. The anterior holding element may be placed at the level of the mitro-aortic junction.

In certain embodiments as shown in FIG. 17, the locking system may be released and connecting element length may be adjusted as many times as necessary. The adjustment may be done during the implant procedure and/or during a second or subsequent procedure. The second or subsequent procedure may be done after days, months or years.

In another embodiment, at least one of the wires may change its profile according to the direction of blood flow. FIG. 18 presents a left atrial view. During ventricular filling the wire may have a very low profile to facilitate the blood flow as shown in FIG. 18A. During ventricular contraction the wire may increase its profile as shown in FIG. 18B, improving mitral regurgitation correction and reducing mechanical stress on mitral valve leaflets.

Certain embodiments may provide advantages over the prior art. For example, certain embodiments may allow treatment of mitral valve regurgitation without open-heart surgery. Mitral valve repair or replacement generally is accomplished by a major open-heart surgical procedure, requiring general anesthesia, full cardiopulmonary bypass with complete cessation of cardiopulmonary activity, seven to ten days of hospitalization and months of recuperation time. The mortality rate with this type of procedure is about five to six percent.

One commonly employed repair technique in open-heart surgery involves the use of annuloplasty rings. An annuloplasty ring has a diameter that is less than the diameter of the enlarged valve annulus. The ring is placed in the valve annulus and the tissue of the annulus sewn or otherwise secured to the ring. This causes a reduction in the annular circumference and an increase in the leaflet coaptation area.

Endovascular heart procedures, in contrast to open heart surgical procedures, would require only local anesthesia, no cardiac bypass, one to two days hospitalization, and should have a reduced mortality rate as compared to open heart procedures.

Therefore, effective techniques that could improve valve function without the need for cardiopulmonary bypass may be advantageous. In particular, passive techniques to change the shape of the valve reducing regurgitation while maintaining substantially normal leaflet motion may be desirable. In addition, a technique that can be employed on a beating heart would allow the practitioner an opportunity to assess the efficacy of the treatment and address any inadequacies without the need for additional bypass support.

However, as discussed in the literature, there are limited possibilities to achieve effective endovascular correction of mitral regurgitation. Existing devices and techniques such as Mitraclip System (Abbott), Cardioband (Valtech Cardio) and Carillon (Cardiac Dimensions) have provided limited evidence of clinical benefit, mainly because they failed to achieve a significant increase in leaflets coaptation. Certain embodiments of the present invention overcome the disadvantages of the foregoing techniques.

For the first time it is possible to increase leaflets coaptation similarly to the technique used in open-heart surgery, using only a transcatheter approach.

Certain embodiments employ the novel method of using wires crossing the orifice of the mitral valve, which was not previously recommended due to potential mitral leaflets damage. The use of wires having the profile changing over the cardiac cycle should minimize leaflets damage.

While the above description contains many specifics, these should not be construed as limitations on the scope of the invention, but rather as an exemplification of preferred embodiments thereof. The invention includes any combination or subcombination of the elements from the different species and/or embodiments disclosed herein. One skilled in the art will recognize that these features, and thus the scope of the present invention, should be interpreted in light of the following claims and any equivalents thereto.

I claim:

1. A method of inserting an annuloplasty device, comprising:
    (1) placing a first holding element into a coronary sinus of a heart;
    (2) connecting one or more connecting elements to the first holding element;
    (3) pulling at least one of the one or more connecting elements to increase mitral valve leaflet coaptation;
    (4) placing a second holding element at the level of the mitro-aortic junction and fibrous trigon of the heart below the aortic valve and connecting the one or more connecting elements to the second holding element.

2. The method of claim 1, wherein the step of connecting one or more connecting elements to the first holding element comprises placing one or more connecting elements through the mitro-aortic junction of the heart.

3. The method of claim 1, wherein the step of connecting the one or more connecting elements to the first holding element comprises:
    piercing the left ventricle outflow tract at the level of fibrous trigon with a first connecting element;
    extending the first connecting element across a valve area towards the posterior mitral annulus of the heart;
    piercing the mitral annulus and the coronary sinus with the first connecting element and connecting the first connecting element to the first holding element.

4. The method of claim 1, wherein one of the one or more connecting elements is placed in the left ventricle outflow tract at the level of the fibrous trigon, below the aortic valve using endovascular techniques.

5. The method of claim 1, wherein at least one of the one or more connecting elements changes its profile during a cardiac cycle to prevent mitral leaflet damage due to impingement of one or more mitral valve leaflets on the at least one connecting element during ventricular systole.

6. The method of claim 1, wherein at least one of the one or more connecting elements changes its profile during a cardiac cycle and does not block blood flow from atrium to ventricle.

7. The method of claim 1, further comprising adjusting the length of one of the one or more connecting elements.

8. The method of claim 7, wherein the step of adjusting the length of one of the one or more connecting elements is performed during a selected one of an initial procedure to install the annuplasty device and a later procedure after the initial procedure is completed.

* * * * *